US012779079B2

(12) United States Patent
Sivagaminathan et al.

(10) Patent No.: US 12,779,079 B2
(45) Date of Patent: Nov. 3, 2026

(54) SYSTEM AND METHOD FOR CREATING DIGITIZED AROMA

(71) Applicant: Givaudan SA, Vernier (CH)

(72) Inventors: Rahul Karthik Sivagaminathan, Blue Ash, OH (US); Adam Eli Cronstein, Cincinnati, OH (US); Joseph Andrew Kaiser, Alexandria, KY (US); Yong Hua Xu, Mason, OH (US)

(73) Assignee: Givaudan SA, Vernier (CH)

( * ) Notice: Subject to any disclaimer, the term of this patent is extended or adjusted under 35 U.S.C. 154(b) by 821 days.

(21) Appl. No.: 17/290,169

(22) PCT Filed: Nov. 4, 2019

(86) PCT No.: PCT/EP2019/080072
§ 371 (c)(1),
(2) Date: Apr. 29, 2021

(87) PCT Pub. No.: WO2020/094556
PCT Pub. Date: May 14, 2020

(65) Prior Publication Data

US 2021/0386898 A1 Dec. 16, 2021

Related U.S. Application Data

(60) Provisional application No. 62/756,348, filed on Nov. 6, 2018.

(51) Int. Cl.

| | |
|---|---|
| ***A61L 9/12*** | (2006.01) |
| ***G06F 3/16*** | (2006.01) |
| ***H04W 4/80*** | (2018.01) |

(52) U.S. Cl.
CPC .............. *A61L 9/125* (2013.01); *G06F 3/167* (2013.01); *H04W 4/80* (2018.02); *A61L 2209/111* (2013.01); *A61L 2209/133* (2013.01)

(58) Field of Classification Search
CPC ............... A61L 9/125; A61L 2209/111; A61L 2209/133; H04W 4/80; G06F 3/167
(Continued)

(56) References Cited

U.S. PATENT DOCUMENTS

| | | | |
|---|---|---|---|
| 7,601,297 B2 | 10/2009 | Gygax | |
| 2005/0244307 A1* | 11/2005 | Gygax | ...................... A61L 9/04 422/123 |

(Continued)

FOREIGN PATENT DOCUMENTS

| | | |
|---|---|---|
| EP | 3147890 A1 | 3/2017 |
| WO | 2018022562 A1 | 2/2018 |

(Continued)

OTHER PUBLICATIONS

International Search Report for Application No. PCT/EP2019/080072 dated Dec. 9, 2019.

(Continued)

*Primary Examiner* — Kevin Edward Schwartz
(74) *Attorney, Agent, or Firm* — Curatolo Sidoti & Trillis Co. LPA; Salvatore A. Sidoti; Floyd Trillis, III

(57) ABSTRACT

A real-time interactive collaboration system for aroma creation is provided. The system includes an aroma blending device adapted to deliver at least one aroma substance to the nasal cavities of a consumer; a plurality of aroma substance containing cartridges including a communication means for data communication between the cartridges and the aroma blending device; a web enabled device that stores a computer algorithm; and a cloud server that stores information related to an aroma creation session. The web enabled device is in communication with the cloud server and the aroma blending device.

13 Claims, 3 Drawing Sheets

(58) Field of Classification Search
USPC .............................................................. 239/34
See application file for complete search history.

(56) References Cited

U.S. PATENT DOCUMENTS

| | | | | |
|---|---|---|---|---|
| 2007/0258849 | A1 | 11/2007 | Kent | |
| 2013/0002405 | A1 * | 1/2013 | Pesonen | H04B 5/00 340/10.5 |
| 2017/0076403 | A1 * | 3/2017 | Edwards | A61L 9/04 |
| 2017/0091504 | A1 * | 3/2017 | Tonnelier | H04L 9/3226 |
| 2017/0253338 | A1 * | 9/2017 | Fantuzzi | B64D 11/00 |
| 2018/0071425 | A1 * | 3/2018 | Jin | A61L 9/127 |
| 2018/0169288 | A1 * | 6/2018 | Kelsen | A61L 9/14 |
| 2018/0369442 | A1 * | 12/2018 | Kelsen | G06K 7/10297 |
| 2020/0324011 | A1 * | 10/2020 | Jin | A61L 9/14 |
| 2021/0100923 | A1 * | 4/2021 | Gimeno Asin | B01F 33/8442 |

FOREIGN PATENT DOCUMENTS

| | | | | |
|---|---|---|---|---|
| WO | WO-2018108587 | A1 * | 6/2018 | A61L 9/01 |
| WO | 2018178320 | A1 | 10/2018 | |
| WO | 2015130347 | A1 | 9/2019 | |

OTHER PUBLICATIONS

Written Opinion of the International Searching Authority for Application No. PCT/EP2019/080072 dated Dec. 9, 2019.

Great Britain Search Report for Application No. 1819675.8 dated May 28, 2019.

YouTube Video, Jul. 17, 2015, available at: www.youtube.com/watch?v=To5EGusthRk.

www.ibtimes.co.uk/ophone-now-you-can-send-smells-around-world-via-smartphone-internet-1453216; Mary-Ann Russon, Now You Can Send Smells Around the World Via Smartphone and the Internet, International Business Times, Jun. 18, 2014.

* cited by examiner

SYSTEM AND METHOD FOR CREATING DIGITIZED AROMA

CROSS REFERENCE TO RELATED APPLICATIONS

This application is a national stage application of International Application No. PCT/EP2019/080072, filed 4 Nov. 2019, which claims priority from U.S. Provisional Patent Application No. 62/756,348, filed 6 Nov. 2018, both of which applications are incorporated herein by reference.

TECHNICAL FIELD

The present disclosure relates to a real-time, interactive collaboration system for aroma creation. More particularly, the present disclosure relates to a real-time interactive system to digitize aroma. Even more particularly, the present disclosure relates to techniques, methods, systems and mechanisms for recording or capturing the multisensorial process of aroma creation.

BACKGROUND

Traditional aroma creation and presentation has typically been carried out using scent bottles, test subjects and/or olfactometers. However, as companies become more global and work schedules more flexible, flavorists and perfumers working together on projects using an aroma blending device are not always located in the same place as each other or in the same place as the aroma blending device. Add in the complexity of also working together with global customers and scheduling creation sessions and consumer studies becomes increasingly difficult.

Accordingly, when creating aromas there is a need for the ability to digitize the aroma, share, collaborate and interact in real-time using near field communication devices and the internet.

SUMMARY

In one embodiment, a real-time interactive collaboration system for aroma creation is provided. The system includes an aroma blending device adapted to deliver at least one aroma substance to the nasal cavities of a consumer; a plurality of aroma substance containing cartridges including a communication means for data communication between the cartridges and the aroma blending device; a web enabled device that stores a computer application; and a cloud server that stores information related to an aroma creation session. The web enabled device is in communication with the cloud server and the aroma blending device.

In another embodiment, a plurality of aroma substance containing cartridges for use with an aroma blending device is provided. The plurality of cartridges include a reservoir for each cartridge, each reservoir containing an aroma substance and inlet and outlet channels to permit ingress of a carrier gas into the reservoir and egress of aroma substance containing carrier gas from the reservoir; and a near field communication (NFC) tag that is configured with information associated with the cartridges. The cartridges communicate with the aroma blending device using NFC.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

Figure 1:
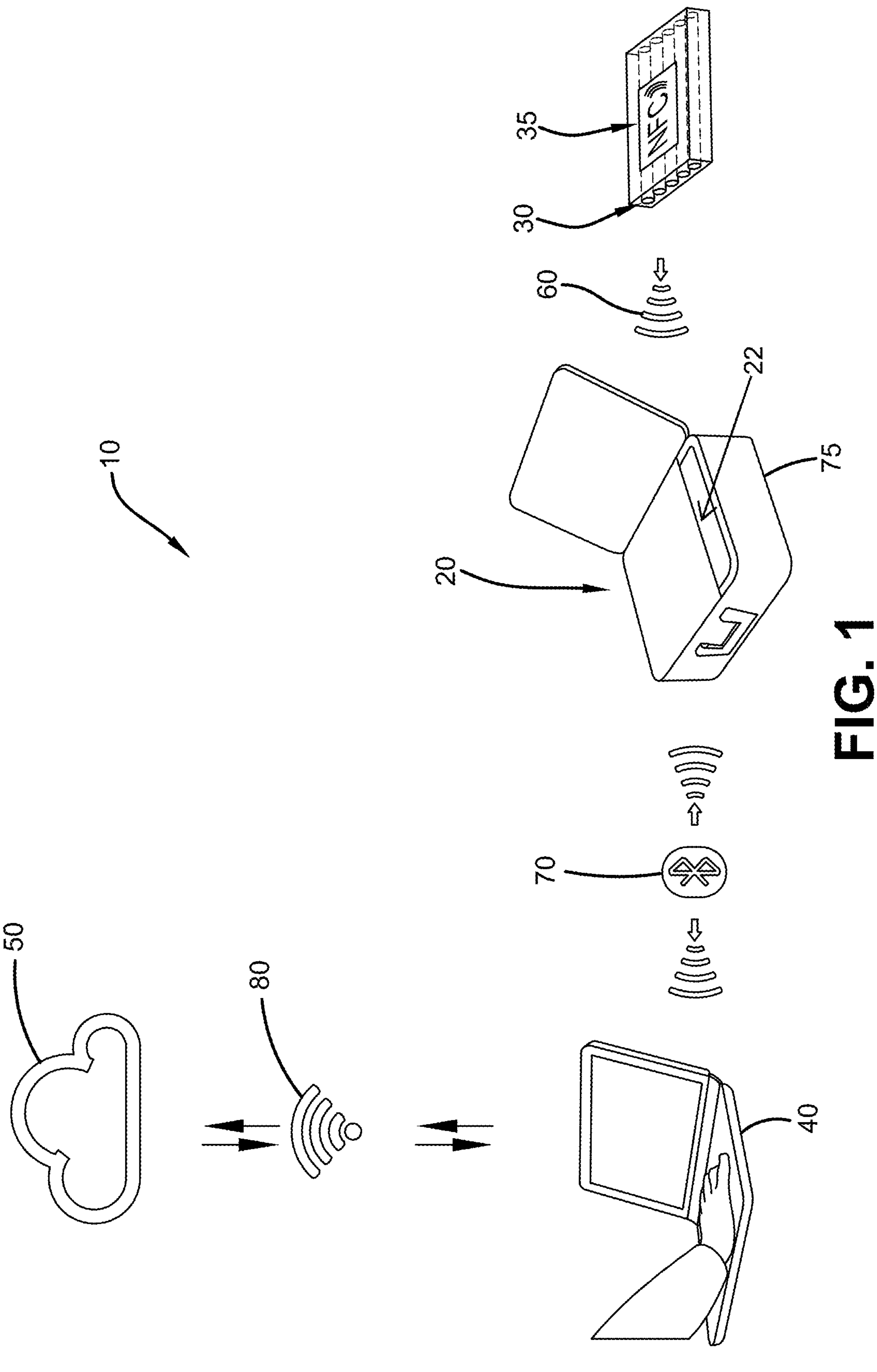
FIG. 1 depicts a real-time interactive collaboration system for aroma creation according to embodiments shown and described herein.

The embodiments set forth in the drawings are illustrative in nature and not intended to be limiting of the disclosure defined by the claims. Moreover, individual features of the drawings and disclosure will be more fully apparent and understood in view of the detailed description.

DETAILED DESCRIPTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

The present disclosure describes various embodiments of a real-time interactive collaboration system 10 for sharing an aroma creation session between users. The system 10 enables users to share, collaborate and interact in real-time. The users may be physically collocated in the same venue, such as, for example, a conference room or lab, or located remotely. In one embodiment, such a system 10 includes an aroma blending device 20; a plurality of aroma substance containing cartridges 30; a web enabled device 40 that stores a computer algorithm and a cloud server 50 that stores session information.

Turning to FIG. 1, is an illustration of a near field communication (NFC) interface enabled aroma blending device 20 communicating with the NFC sticker(s) 35 attached to the aroma substance containing cartridges 30 and the web enabled device 40 in accordance with one embodiment of the present disclosure. In one embodiment, web enabled device 40 is also communicating with the cloud server 50 over the internet.

In accordance with one embodiment, the aroma blending device 20 may include the following elements (not all elements are shown): a source of carrier gas flow; a regulating means which receives the carrier gas flow and regulates its passage through a plurality of channels; downstream of the regulating means, a plurality of aroma substance containing cartridges 30, one being associated with each channel; and a disseminating means adapted to deliver at least one aroma substance to the nasal cavities of a consumer. In one embodiment, the aroma blending device 20 may be an olfactometer device (an instrument capable of exactly dosing a portion of a gaseous phase which is present due to the vapor pressure of a sample or in the form of a liquid or a solid) for example the Virtual Aroma Synthesizer® device or MiniVAS™ device, both developed and owned by Givaudan.

The source of carrier gas may be any suitable source of gas. For example, the carrier gas may be air or nitrogen, and the source may be a compressor. Alternatively, the source may be a pressurized cylinder of gas. The gas flow is conveyed to a regulating means. The regulating means is typically a device that comprises a plurality of channels adapted to convey the gas to cartridges 30 containing aroma substance, one cartridge per channel. Thus, by opening and closing channels and maintaining these openings and closings for predetermined times, the regulating means can determine which aroma substances and how much thereof are conveyed and when, and thus alter the nature of the aroma perceived by a user.

The operation of the regulating means may be remote, for example, by computer either wired to the regulating device or operating it wirelessly. In one embodiment, the aroma blending device 20 includes a short range communication reader 22 for short range communication. Non-limiting examples of short range communication include, Bluetooth, radio frequency identification (RFID), infrared data association (IrDA), ultra wideband (TJWB), ZigBee, or any number of other wireless communication protocols or interfaces. In one embodiment, the aroma blending device includes a NFC interface. The NFC interface may have a range of approximately about 4 inches to about 8 inches. The close range communication with the NFC interface may take place via magnetic field induction 60, allowing the NFC interface to communicate with other NFC device or to retrieve information from an NFC sticker(s) 35 located on the plurality of cartridges 30 as explained in more detail below.

In accordance with another embodiment, the aroma blending device 20 may have a display 25. Display may function as a touch screen through which a user may interact with the aroma blending device 20.

Figure 2A:
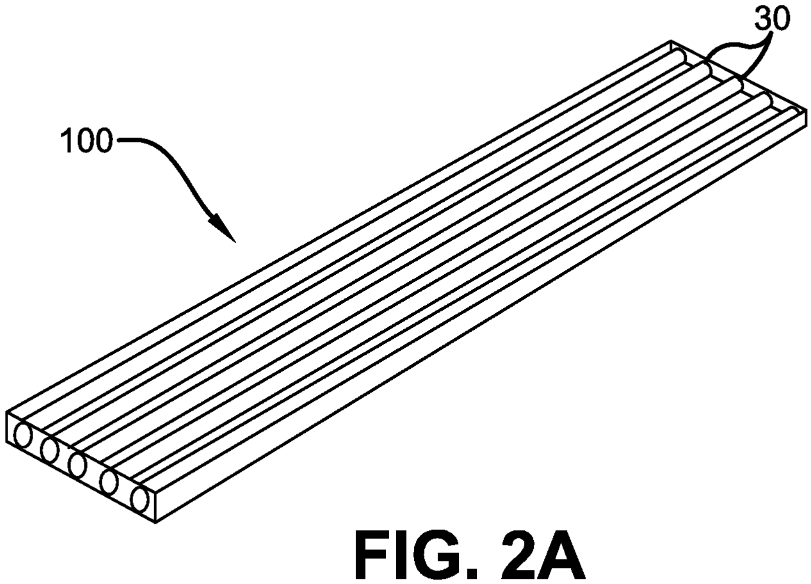
FIG. 2*a* depicts a schematic perspective view of a support body containing a plurality of cartridges within the support body according to embodiments shown and described herein.
Figure 2B:
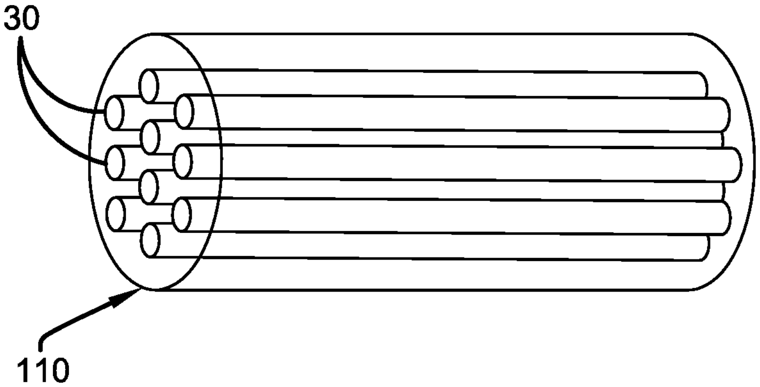
FIG. 2*b* depicts a schematic perspective view of a support body containing a plurality of cartridges within the support body according to embodiments shown and described herein.

The cartridges 30 of aroma substance from which the desired aroma is created may be any suitable cartridge capable of containing the desired aroma substances and releasing them when impinged upon by a carrier gas. One particular type is a cartridge 30 comprising a reservoir containing an aroma substance and being provided with inlet and outlet channels to permit ingress of carrier gas into the reservoir and egress of aroma substance-containing carrier gas from the reservoir, the channels being defined by capillaries having internal diameter and length dimensions sufficient to act as closure means to prevent, or substantially prevent, leakage of aroma substance from the reservoir into a head space external of the cartridge when carrier gas flow is interrupted. Such a cartridge is described in U.S. Pat. No. 7,601,297, incorporated herein by reference in its entirety. It has the advantages that it can be small and very slim (about credit card-sized) and that it need no valve arrangements, merely a supply of carrier gas to entrain the substance from the cartridge and means of directing and regulating this. Such cartridges are easily replaced when empty. FIG. 2*a* shows a credit-card design 100 for a support body in perspective containing a plurality of cartridges 30 or rack. In another embodiment, FIG. 2*b* shows a generally cylindrical support body 110 containing a plurality of cartridges 30 or rack. In one embodiment, a rack consists of any number of individual cartridges including, for example, 3, 4, 5, 6, 7, 8, 9, 10, 11, 12, 13, 14, 15 or more cartridges. In some embodiments, the rack of cartridges includes at least five individual cartridges; in another embodiment at least 10 individual cartridges; in another embodiment at least fifteen individual cartridges. In another embodiment, the aroma blending device may include more than 1 rack of cartridges, for example at least 2 or 3 racks of cartridges, for the possibility of a total of 30 or 45 individual cartridges loaded into the aroma blending device 20.

The aroma substances that are entrained by the gas flow from the cartridges are conveyed by the carrier to a disseminating means via a conduit. The nature of the disseminating means may be any disseminating means capable of delivering a vapour-phase substance to the nasal cavities of an individual. For example, it may be a small nose piece able to be worn, or it may be a sniffing port connected to the aroma blending device.

Each plurality or rack of cartridges 30 would have a pre-programmed, unique NFC sticker or tag 35 that is configured with a predetermined identifier for security and for storing data associated with one or more operating parameters of the cartridges. Once the rack of cartridges 30 is inserted into the aroma blending device 20 and the identifier is validated, the aroma blending device 20 is activated. In one embodiment, without the validation of the NFC sticker 35, the aroma blending device 20 would not be operational. This ensures that only authenticate and valid cartridges 30 can be used with the aroma blending device 20. In another embodiment, the validation of the NFC sticker 35 is optional.

In one embodiment, the type of information that is stored on the NFC sticker 35 and subsequently retrieved by the aroma blending device 20 includes a security code or identifier that is unique to the rack of cartridges 30 that it is attached. Other information that is stored on the NFC sticker 35 includes an expiration date for the rack and specific ingredient information for each cartridge (for example, which aroma chemicals are loaded in the cartridge), date and time stamp information or if the amount of data is too large, a link to a cloud server in order to retrieve the aroma substance information. During use, additional information may be stored on the NFC stickers 35 including usage information, for example, amount of air flow or flow-rate, duration of usage, expiry date of cartridges 30.

In accordance with the present disclosure, the system 10 may also include a web enabled device 40 in order to access the Internet. As used herein, the term web enabled device 40 refers to any portable device capable of running one or more software applications and also can be connected to the Internet or one or more computer networks. Web enabled devices 40 include, but are not limited to, personal computers, laptop computers, smartphones (for example, iPhone or Android), tablets, netbooks, GPS devices, e-readers, iPads, smart TV's and mobile game consoles (for example, Nintendo DS, Sony PSP). In accordance with one embodiment, the web enabled device 40 is in communication with the cloud server 50 and the aroma blending device 20.

The web enabled device 40 may include at least one central processing unit (CPU). The CPU may provide processing capability to execute an operating system, run various applications, and/or provide processing for one or more of the techniques described herein. Applications may include, for example, software for blending of the aroma substances. An example of such software is Aroma Composer™ Software developed by Givaudan Flavors Corporation of Cincinnati, Ohio. The Aroma Composer™ Software controls the ratios and intensities of the ingredient samples or aroma substances delivered to the sniffing port for evaluation by a consumer. In another embodiment, software that uses data science and predictive analytics to analyze data collected from consumers is included. An example of such software is ATOM™ Software developed by Givaudan Flavors Corporation of Cincinnati, Ohio.

A main memory may be communicably coupled to the CPU, which may store data and executable code. The main memory may represent volatile memory such as RAM, but may also include nonvolatile memory, such as read-only memory (ROM) or Flash memory. In buffering or caching data related to operations of the CPU, the main memory may store data associated with applications running on the web enabled device 40.

The web enabled device 40 may also include nonvolatile storage. The nonvolatile storage may represent any suitable nonvolatile storage medium, such as a hard disk drive or nonvolatile memory, such as Flash memory. Being well-suited to long-term storage, the nonvolatile storage may store data files.

One or more network interfaces may exist on the web enabled device for network connectivity. The network interface may be any network including, but not limited to, a telephone network or a computer network (e.g., the internet, a local area network, a wide area network, and/or wireless network such as a cellular network, a Wi-Fi network according to Institute of Electrical and Electronics Engineers (IEEE) standards 802.11a/b or g or other such wireless local area network standards, or a WiMax network according to IEEE standard 802.16 or another such wireless broadband standard). In another embodiment, the web enabled device 40 includes a Bluetooth communication interface 70 and a microphone to capture audio.

In accordance with the present disclosure, the system 10 may also include a cloud server 50 for storing information related to an aroma creation session, for example, aroma substance specific information. A cloud server 50 is a logical server that is built, hosted and delivered through a cloud computing platform over the Internet 80. Cloud servers 50 possess and exhibit similar capabilities and functionality to a typical server but are accessed remotely from a cloud service provider. In other words, cloud servers 50 can be configured to provide levels of performance, security and control similar to those of a dedicated server. But instead of being hosted on physical hardware that's solely used by you, they reside in a shared "virtualized" environment that's managed by your cloud hosting provider. According to one embodiment, cloud server 50 includes memory and a processor. The memory stores information, for example, ingredient information and session information, while the processor updates the NFC sticker 35.

In one embodiment, the communication between the web enabled device 40 and the cloud server 50 and the web enabled device 40 and the aroma blending device 20 enables a platform for users to share key learnings. Additionally, this communication enables a unique record session feature which allows users to capture and replay the process of aroma substance creation in a multisensorial dimension (aroma, audio and screen capture). For example, this feature may be used to record the proposed aroma substance created by a flavorist(s), the reaction and feedback of a customer(s) 220, the real-time changes to the aroma substance made by the flavorist(s) in response to input and feedback of a customer and to bookmark important aroma substances during the creation process to allow a user to jump to that specific point in time during playback of a session. In another embodiment, the real-time, interactive collaboration system 10 may include multiple aroma blending devices 20 and multiple web enabled devices 40 (in different locations networked together) through the internet 80. This would allow users located in remote locations to experience the same aroma profile during for example, a creation or working session.

Figure 3:
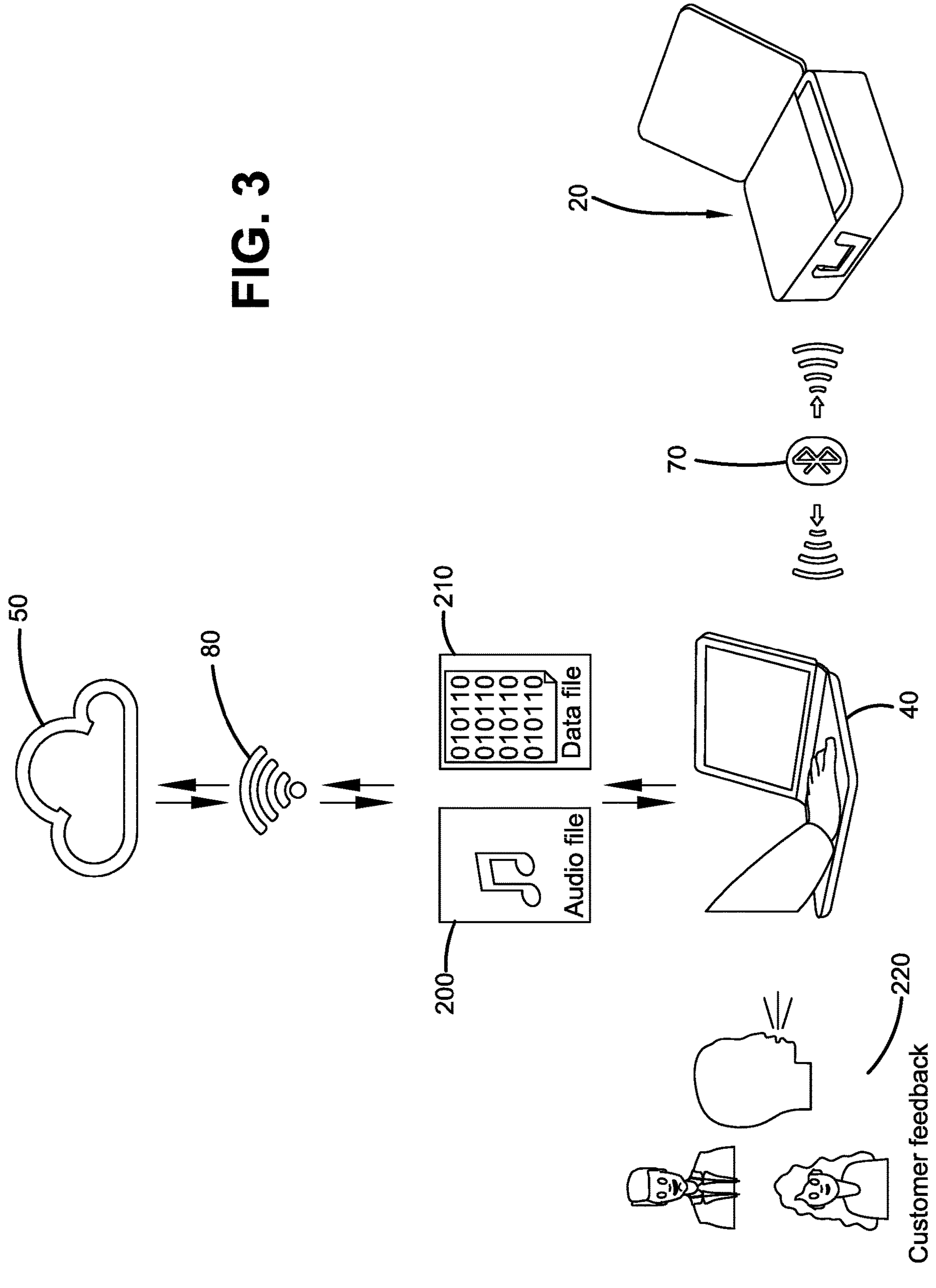
FIG. 3 depicts a record session feature of a real-time interactive collaboration system for aroma creation according to embodiments shown and described herein.

With reference to FIG. 3, features allowing the system 10 to record a session in real-time are further described. In one embodiment, the web enabled device 40 contains software, for example, Aroma Composer™ software that controls the aroma blending device 20. In another embodiment, the software also has the ability to record both audio feedback via a microphone in the web enabled device 40 and session data (collectively "session recording"). For example, the audio feedback is recorded and saved via audio files 200 or data files 210, for example, an audio file and the session data such as mouse clicks, flow rates, time increments, or bookmarks, are saved in one embodiment as a data file such as a Java Script Object Notation (JSON) file. In one embodiment, the session recording does not contain any ingredient specific information about what aroma substances are loaded in the cartridges. Rather, the aroma substance specific information may be stored on the cloud server 50 via a session file. In one embodiment, each session recording is linked to a session file.

Presently, NFC stickers 35 can only hold a relatively small amount of data (KB size). As technology improves and NFC stickers 35 are capable of holding data of several MB size, the need to have a cloud server to store session files will be eliminated. Rather, all of the session files and session recording data will be able to be stored on the NFC sticker 35.

In the broadest sense, the present disclosure describes a system that for capturing the digital signature of an aroma, storing it digitally and retrieving it on demand, i.e. technology for digitizing aroma. The digitized form of aroma can be stored digitally, transmitted to users via email and other digital means, and reproduced via the web enabled device 40 and the aroma blending device 20. For example, a flavor or fragrance formulation is stored on cloud server 50 as data; the data is sent to the web enabled device 40 having software for analyzing the formulation(s); and then the web enabled device 40 communicates with the aroma blending device 20 in order to convert the formulation into an aroma profile for users to smell with corresponding cartridge 30. When users or consumers identify an aroma profile using the aroma blending device 20 with certain cartridges 25, the aroma profile can be converted into a formula that can be stored in a cloud server 50.

In another embodiment, the communication between the web enabled device 40 and the cloud server 50 and the web enabled device 40 and the aroma blending device 20 may enable consumers to experience aromas corresponding to pictures or videos as part of a presentation, for example a PowerPoint® presentation. In one embodiment, as part of a real-time, interactive aroma creation session, an individual may present a presentation via the web enabled device 40. According to the present disclosure, as the presentation moves from slide to slide showing different pictures or videos, for example a picture of an orange on one slide and a picture of a watermelon on a second slide, the system can be configured such that the aroma blending device 20 creates aromas or aroma blends matching the pictures on the slides for the viewers of the presentation to smell.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A real-time interactive collaboration system for aroma creation between users located in remote locations, comprising:

a plurality of near field communication means enabled aroma blending devices in different locations adapted to deliver at least one aroma substance to nasal cavities of an individual to create a desired aroma from blending of the least one aroma substance, to allow users located in remote locations to experience an aroma profile during an aroma creation session;

one or more racks including a plurality of aroma substance containing cartridges inserted into each aroma blending device of the plurality of aroma blending devices, wherein the one or more racks includes a near field communication means configured with an identifier for security and for storing data associated with one or more operating parameters of the plurality of aroma substance containing cartridges for data communication between the plurality of aroma substance containing cartridges and each aroma blending device of the plurality of aroma blending devices and for activation of the plurality of aroma blending devices;

a plurality of web enabled devices in different locations networked together through the Internet that stores a computer application for blending of the aroma substances by the plurality of aroma blending devices and for recording an aroma creation session in real-time; and a cloud server that stores information related to an aroma creation session;

wherein the plurality of web enabled devices are in communication with the cloud server and the plurality of aroma blending devices, wherein the system enables the users in remote locations to share, collaborate, and interact in real-time during the aroma creation session, and wherein recording of the aroma creation session allows the users located in remote locations to capture and replay a process of aroma creation in a multisensorial dimension.

2. The system according to claim 1, wherein each aroma blending device of the plurality of the aroma blending devices includes a display.

3. The system according to claim 2, wherein the display is a touch screen.

4. The system according to claim 1, wherein each web enabled device of the plurality of web enabled devices includes a microphone.

5. The system according to claim 1, wherein each aroma blending device of the plurality of the aroma blending devices includes a short range communication reader.

6. The system according to claim 5, wherein the near field communication means includes a near field communication (NFC) interface.

7. The system according to claim 1, wherein the information on the cloud server includes aroma substance information for each cartridge of the plurality of aroma substance containing cartridges.

8. The system according to claim 7, wherein the aroma substance information is selected from a group consisting of a security code, ingredient information, a date and time stamp, an expiry date, air flow through cartridges, and duration of usage for cartridges.

9. The system according to claim 1, wherein the computer application includes a record session feature for recording the aroma creation session.

10. The system according to claim 1, wherein the plurality of aroma substance containing cartridges includes at least 10 cartridges.

11. The system according to claim 1, wherein the plurality of aroma substance containing cartridges includes at least 15 cartridges.

12. The system of claim 1, wherein each aroma blending device of the plurality of aroma blending devices can record a proposed aroma substance created by a use, reaction and feedback of a customer, and real-time changes to the aroma substance made by the users in response to the feedback of the customer.

13. The system of claim 1, wherein the information stored on the cloud server related to an aroma creation session comprises a formulation of an aroma as digitized data, wherein the system can transmit the data to the plurality of web enabled devices, and wherein the plurality of web enabled devices can communicate with the plurality of aroma blending devices to convert the formulation into an aroma profile.

* * * * *